United States Patent
Lietzau et al.

(10) Patent No.: US 10,017,695 B2
(45) Date of Patent: Jul. 10, 2018

(54) FLUORINATED DIBENZOFURAN AND DIBENZOTHIOPHENE DERIVATIVES

(71) Applicant: MERCK PATENT GMBH, Darmstadt (DE)

(72) Inventors: Lars Lietzau, Rossdorf (DE); Constanze Brocke, Gross-Gerau (DE); Volker Reiffenrath, Rossdorf (DE); Atsutaka Manabe, Bensheim (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 15/095,229

(22) Filed: Apr. 11, 2016

(65) Prior Publication Data
US 2016/0298034 A1   Oct. 13, 2016

(30) Foreign Application Priority Data
Apr. 13, 2015   (DE) .................. 10 2015 004 505

(51) Int. Cl.
G02F 1/1333 (2006.01)
C09K 19/34 (2006.01)
C07D 307/91 (2006.01)
C07D 333/76 (2006.01)

(52) U.S. Cl.
CPC ........ C09K 19/3491 (2013.01); C07D 307/91 (2013.01); C07D 333/76 (2013.01); C09K 19/3405 (2013.01); C09K 2019/3408 (2013.01)

(58) Field of Classification Search
CPC ............ G02F 1/1333; C09K 19/3491; C09K 19/3402; C09K 2019/3408; C07D 307/91; C07D 333/76
USPC ...................................... 252/299.61; 428/1.1
See application file for complete search history.

(56) References Cited

U.S. PATENT DOCUMENTS

| | | | | |
|---|---|---|---|---|
| 7,018,685 B2 * | 3/2006 | Schmidt | .................. | C07C 25/22 252/299.61 |
| 7,255,900 B2 * | 8/2007 | Schmidt | ............... | C07D 307/91 252/299.61 |
| 7,514,127 B2 * | 4/2009 | Lietzau | .................. | C07C 25/22 252/299.61 |
| 9,512,102 B2 * | 12/2016 | Reiffenrath | .......... | C07D 409/04 |
| 2005/0258399 A1 | 11/2005 | Schmidt et al. | | |

FOREIGN PATENT DOCUMENTS

| | | |
|---|---|---|
| DE | 102004021691 A1 | 11/2005 |
| DE | 102005012585 A1 | 11/2005 |
| WO | 02/055463 A1 | 7/2002 |

OTHER PUBLICATIONS

European Search Report dated Sep. 14, 2016, issued in corresponding EP Application No. 16000733, 6 pages.
English translation Abstract of DE102005012585A1 published Nov. 3, 2005 (2 page).
English translation Abstract of DE102004021691A1 published Nov. 24, 2005 (2 page).
English translation Abstract of WO02055463A1 published Jul. 18, 2002 (2 page).

* cited by examiner

*Primary Examiner* — Geraldina Visconti
(74) *Attorney, Agent, or Firm* — Millen White Zelano and Branigan, PC; John Sopp

(57) ABSTRACT

Disclosed are dibenzofuran and dibenzothiophene derivatives of the general formula I,

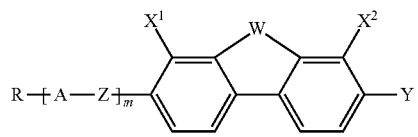

in which $X^1$, $X^2$, W, Y, R, A, Z and m have the meaning defined in claim 1, to a process for the preparation thereof, to the use thereof as components in liquid-crystalline media, and to electro-optical display elements which contain the liquid-crystalline media according to the invention.

11 Claims, No Drawings

FLUORINATED DIBENZOFURAN AND DIBENZOTHIOPHENE DERIVATIVES

FIELD OF THE INVENTION

The present invention relates to fluorinated dibenzofuran and dibenzothiophene derivatives, to a process for the preparation thereof, to liquid-crystal (LC) media comprising these derivatives, and to electro-optical display elements containing these liquid-crystalline media.

BACKGROUND OF THE INVENTION

Liquid crystals have found widespread use since the first commercially usable liquid-crystalline compounds were found about 30 years ago. Known areas of application of conventional mixtures are, in particular, displays for watches and pocket calculators, and large display panels as used in railway stations, airports and sports arenas. Further areas of application are displays of portable and desktop computers, navigation systems and video applications. For the last-mentioned applications in particular, high demands are made of the response times and contrast of the images.

The spatial arrangement of the molecules in a liquid crystal has the effect that many of its properties are direction-dependent. Of particular importance for use in liquid-crystal displays are the optical, dielectric and elastomechanical anisotropies. Depending on whether the molecules are oriented with their longitudinal axes perpendicular or parallel to the two plates of a capacitor, the latter has a different capacitance; in other words, the di-electric constant ε of the liquid-crystalline medium has different values for the two orientations. Substances whose dielectric constant is larger when the longitudinal axes of the molecules are oriented perpendicular to the capacitor plates than when they are oriented parallel are referred to as dielectrically positive. In other words, if the dielectric constant $\varepsilon_{\parallel}$ parallel to the longitudinal axes of the molecules is larger than the dielectric constant $\varepsilon_{\perp}$ perpendicular to the longitudinal axes of the molecules, the dielectric anisotropy $\Delta\varepsilon=\varepsilon_{\parallel}-\varepsilon_{\perp}$ is greater than zero. Most liquid crystals used in conventional displays fall into this group.

Both the polarisability of the molecule and the permanent dipole moment play a role for the dielectric anisotropy. On application of a voltage to the display, the longitudinal axis of the molecules orients itself in such a way that the larger of the dielectric constants becomes effective. The strength of the interaction with the electric field depends on the difference between the two constants.

In the case of the liquid-crystalline molecules used in conventional liquid-crystal displays, the dipole moment oriented along the longitudinal axis of the molecules is greater than the dipole moment oriented perpendicular to the longitudinal axis of the molecules.

By means of liquid crystals in which the greater dipole moment is oriented parallel to the longitudinal axis of the molecule, very high-performance displays have already been developed. In most cases here, mixtures of from 5 to 20 components are used in order to achieve a sufficiently broad temperature range of the mesophase and short response times and low threshold voltages. However, difficulties are still caused by the strong viewing angle dependence in liquid-crystal displays as are used, for example, for laptops. The best imaging quality can be achieved if the surface of the display is perpendicular to the viewing direction of the observer. If the display is tilted relative to the observation direction, the imaging quality deteriorates drastically under certain circumstances. For greater comfort, attempts are being made to maximise the angle through which the display can be tilted from the viewing direction of an observer without significantly reducing the imaging quality. Attempts have recently been made to improve the viewing-angle dependence using liquid-crystalline compounds whose dipole moment perpendicular to the longitudinal axis of the molecule is larger than that parallel to the longitudinal axis of the molecule. The dielectric anisotropy $\Delta\varepsilon$ is negative in this case. In the field-free state, these molecules are oriented with their longitudinal axis perpendicular to the glass surface of the display. Application of an electric field causes them to orient themselves more or less parallel to the glass surfaces. In this way, it has been possible to achieve an improvement in the viewing-angle dependence. Displays of this type are known as VA-TFT ("vertically aligned") displays.

Development in the area of liquid-crystalline materials is still far from complete. In order to improve the properties of liquid-crystalline display elements, attempts are constantly being made to develop novel compounds which enable optimisation of such displays.

It is an object of the present invention to provide compounds having advantageous properties for use in liquid-crystalline media. In particular, they should have negative dielectric anisotropy, which makes them particularly suitable for use in liquid-crystalline media for VA displays. Irrespective of the dielectric anisotropy corresponding to the display type, compounds are desired which have a favourable combination of the applicational parameters. Of these parameters, which are to be optimised simultaneously, particular mention should be made of a high clearing point, a low rotational viscosity, an optical anisotropy in the use range, and the properties which serve to achieve mixtures having the desired liquid-crystalline phases over a broad temperature range (lower melting point, good miscibility with other liquid-crystalline components of the desired type).

Further LC display modes, which are also used, in particular, for small and medium-sized LC displays for use in portable devices, such as, for example, tablet PCs or so-called smartphones, are the IPS mode and the FFS (fringe field switching) mode, in which LC media having positive dielectric anisotropy are used. The prior art discloses that the properties of a liquid-crystal display of the FFS type can be improved by adding liquid-crystal materials having negative dielectric anisotropy to highly polar LC media having positive dielectric anisotropy, causing the dielectric constant $\varepsilon\perp$ perpendicular to the longitudinal molecular axes of the LC mixture to be increased (see EP 2 628 779 A2). Consequently, the high negative dielectric anisotropy of the admixed substances must be compensated again by a higher proportion of materials having positive dielectric anisotropy in order to produce the polarity of the mixture which is necessary for switching. There is therefore a need for LC mixture components which, although having a high $\varepsilon\psi$, reduce the polarity of an LC mixture having positive $\Delta\varepsilon$ to a lesser extent owing to a relatively low $\Delta\varepsilon$.

A further object of the present invention is therefore to provide compounds which, besides the above-mentioned advantageous applicational properties, have particularly high values of $\varepsilon\perp$ at the same time as relatively low values of $\Delta\varepsilon$. In other words, the ratio of $\varepsilon\perp$ to $|\Delta\varepsilon|$ must be as large as possible.

Upon further study of the specification and appended claims, other objects, aspects and advantages of the invention will become apparent. The prior art discloses VA materials which are derived from dibenzofuran or from dibenzothiophene.

WO 02/055463 discloses compounds of the formula

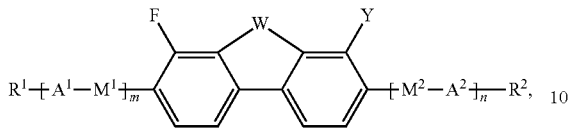

in which X can denote, inter alia, O or S, Y can denote F, R¹ and R² can denote alkyl or alkoxy, and the other parameters have the meaning indicated therein. The compounds described therein have negative dielectric anisotropy, but were developed for ferroelectric LC mixtures and no values for the dielectric anisotropies of the individual substances are described.

Similar compounds are disclosed in DE 10 2004 021 691 A1, in which the group X generically includes polar radicals, such as F or —CF₃, but preferably denotes H.

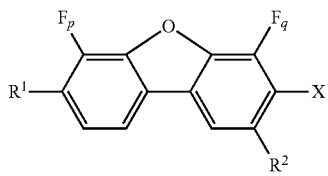

DE 10 2005 012 585 A1 describes, inter alia, dibenzofuran and dibenzothiophene compounds of the general formula

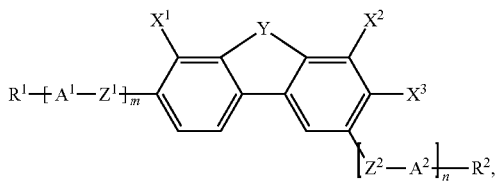

in which, inter alia, Y can denote O or S, the radical R¹ can denote alkoxy, R² can denote H, m and n can denote 0 and the radicals X¹, X² and X³ can denote F, as, for example, in the compound of Example No. 97

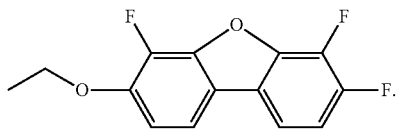 [SMILES: CCOc1ccc2c(oc3c(F)c(F)ccc32)c1F]

The compounds are highly polar and were developed as components for liquid-crystal mixtures for VA displays.

SUMMARY OF THE INVENTION

Surprisingly, it has been found that one or more of the objects described above can be achieved by compounds of the formula I

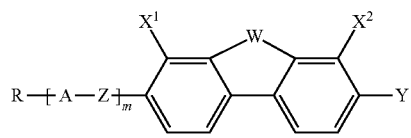

in which
W denotes O or S,
Y denotes F, Cl, CF₃, OCF₃ or OCF₂H,
  with the proviso that, if W denotes O, Y cannot be F,
X¹, X² denote H or F, with the proviso that at least one radical X¹ or X² denotes F,
R denotes an alkyl or alkoxy radical having 1 to 15 C atoms, where, in addition, one or more CH₂ groups in these radicals may each be replaced, independently of one another, by —C≡C—, —CF₂O—, —OCF₂—, —CH=CH—,

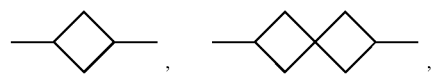

—O—, —CO—O— or —O—CO— in such a way that O atoms are not linked directly to one another, and in which, in addition, one or more H atoms may be replaced by halogen,
  A on each occurrence, identically or differently, denotes a radical selected from the following groups:
    a) 1,4-phenylene, in which, in addition, one or two CH groups may be replaced by N and in which, in addition, one or more H atoms may be replaced by a group L,
    b) the group consisting of trans-1,4-cyclohexylene and 1,4-cyclohexenylene, in which, in addition, one or more non-adjacent CH₂ groups may be replaced by —O— and/or —S— and in which, in addition, one or more H atoms may be replaced by F or Cl, and
    c) the group consisting of tetrahydropyran-2,5-diyl, 1,3-dioxane-2,5-diyl, tetrahydrofuran-2,5-diyl, cyclobutane-1,3-diyl, piperidine-1,4-diyl, thiophene-2,5-diyl and selenophene-2,5-diyl, each of which may also be mono- or polysubstituted by a group L,
  L on each occurrence, identically or differently, denotes F, Cl, CN, SCN, SF₅ or straight-chain or branched, and in each case optionally fluorinated, alkyl, alkoxy, alkylcarbonyl, alkoxycarbonyl, alkylcarbonyloxy or alkoxycarbonyloxy having 1 to 12 C atoms, and
  Z on each occurrence, identically or differently, denotes a single bond, —CF₂O—, —OCF₂—, —CH₂O—, —OCH₂—, —(CO)O—, —O(CO)—, —(CH₂)₄—, —CH₂CH₂—, —CF₂—CF₂—, —CF₂—CH₂—, —CH₂—CF₂—, —CH=CH—, —CF=CF—, —CF=CH—, —CH=CF—, —(CH₂)₃O—, —O(CH₂)₃—, —C≡C—, —O—, —CH₂—, —(CH₂)₃— or —CF₂—,
  m denotes 0, 1 or 2.

The compounds have negative Δε and are therefore suitable, in particular, for use in VA-TFT displays and very particularly as additives in IPS or FFS displays. The compounds according to the invention preferably have a Δε between 0 and −8, particularly preferably between −2 and −4, with values of ε⊥ of preferably >10, particularly preferably >15. The ratio ε⊥/|Δε| is preferably >3, particularly preferably >5. They exhibit good miscibility with the usual substances used in liquid-crystal mixtures for displays, i.e. they have good solubility therein. The rotational viscosity of the liquid-crystalline mixtures comprising the compounds of formula I is preferably 350 mPa·s or less, more preferably 250 mPa·s or less and particularly preferably 150 mPa·s or less. The rotational viscosities of the compounds and of the resultant liquid-crystalline mixtures are advantageously low.

The other physical, physicochemical or electro-optical parameters of the compounds according to the invention are also advantageous for use of the compounds in liquid-crystalline media. The liquid-crystalline media which comprise these compounds have, in particular, an adequate width of the nematic phase and good low-temperature and long-term stability as well as sufficiently high clearing points. The low melting points of the compounds according to the invention give an indication of the advantageous mixing behaviour. Furthermore, the compounds of the formula I according to the invention have values of the optical anisotropy Δn which are suitable, in particular, for use in VA-TFT displays. The compounds according to the invention preferably have a Δn of greater than 0.15 and less than 0.25.

DETAILED DESCRIPTION OF THE INVENTION

Exemplary embodiments of the present invention are described in detail below.

R preferably denotes an alkoxy radical, alkyl radical or alkenyl radical having 1 to 7 or 2 to 7 carbon atoms respectively. R in the general formula I is particularly preferably an alkoxy radical or alkyl radical having 2 to 7 C atoms. In the case where m=0, R preferably denotes an alkoxy group having 1-7 C atoms, particularly preferably having 2 to 5 C atoms.

In the case where m=1 or 2, R preferably denotes an alkyl, alkoxy or alkenyl group, particularly preferably an alkyl or alkenyl group having 1-7 C atoms, particularly preferably having 2 to 5 C atoms.

If R represents an alkyl radical, this is straight-chain or branched. R is preferably straight-chain and, unless indicated otherwise, has 1, 2, 3, 4, 5, 6 or 7 C atoms and is accordingly preferably methyl, ethyl, propyl, butyl, pentyl, hexyl or heptyl.

If R represents an alkoxy radical, this is straight-chain or branched. R is preferably straight-chain and, unless indicated otherwise, has 1, 2, 3, 4, 5, 6 or 7 C atoms and is accordingly preferably methoxy, ethoxy, propoxy, butoxy, pentoxy, hexoxy or heptoxy.

R in formula I can furthermore be an alkenyl radical having 2 to 15 C atoms, which is straight-chain or branched and contains at least one C—C double bond. It is preferably straight-chain and has 2 to 7 C atoms. It is accordingly preferably vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl. If both C atoms of the C—C double bond are substituted, the alkenyl radical can be in the form of the E and/or Z isomer (trans/cis). In general, the respective E isomers are preferred. Of the alkenyl radicals, prop-2-enyl, but-2- or -3-enyl and pent-3- or -4-enyl are particularly preferred.

R in formula I can also be an alkynyl radical having 2 to 15 C atoms, which is straight-chain or branched and contains at least one C—C triple bond. 1- or 2-propynyl and 1-, 2- or 3-propynyl are preferred.

The group A on each occurrence, identically or differently, preferably denotes a disubstituted cyclic group selected from the formulae

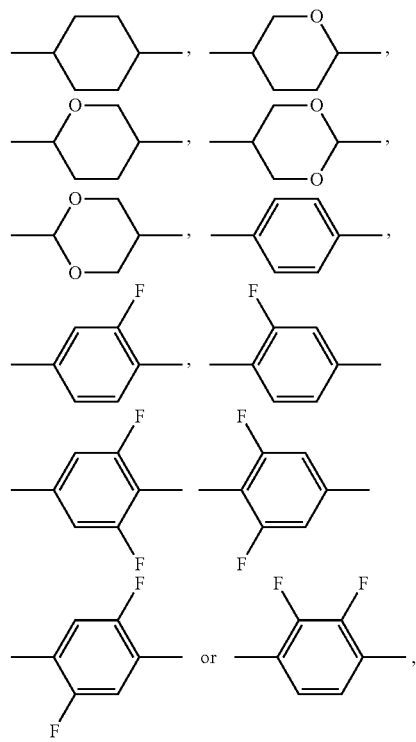

in particular

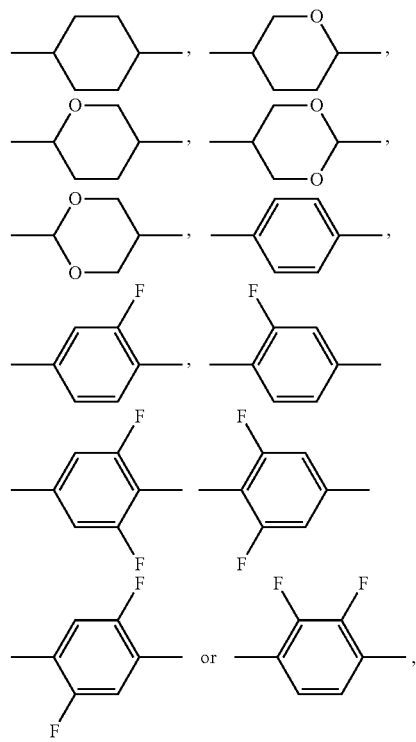

The group Z preferably denotes a single bond, —CH$_2$O—, —CF$_2$O— or —OCF$_2$—, particularly preferably —CH$_2$O—.

The group W preferably denotes O.

For the groups X$^1$ and X$^2$, it is preferred for both to denote F.

The group Y preferably denotes —CF$_3$ or —OCF$_3$, particularly preferably —OCF$_3$.

The group L preferably denotes F, Cl, —CF$_3$ or an alkyl or alkoxy group having 1, 2 or 3 carbon atoms, particularly preferably F.

The parameter m preferably has a value of 0 or 1.

Particularly preferably, m denotes 0 and R denotes an alkoxy group having 1 to 7 carbon atoms.

Halogen in the context of the present invention denotes fluorine, chlorine, bromine or iodine, in particular fluorine or chlorine.

In connection with the present invention, the expression "alkyl"—if not defined otherwise elsewhere in this description or in the claims—denotes a straight-chain or branched, saturated, aliphatic hydrocarbon radical having 1 to 15 carbon atoms.

Particular preference is given to compounds of the formula I according to the invention selected from the sub-formulae Ia to Id,

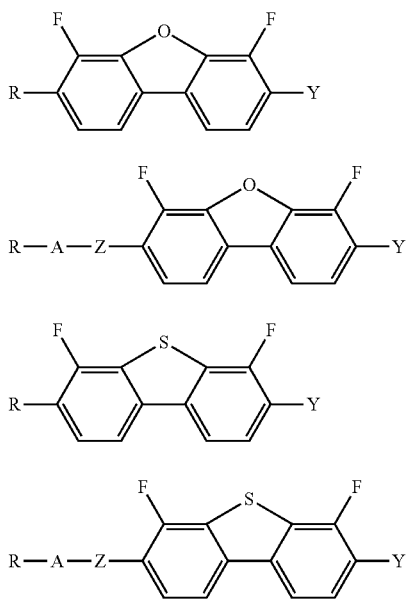

where the radicals R, A, Z and Y have the meanings indicated above.

Preferred compounds of the formulae Ia, Ib, Ic and Id are the compounds of the formulae Ia and Ib having the preferred sub-formulae Ia-1 and Ia-2,

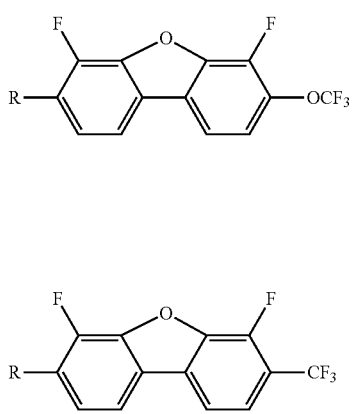

in which R denotes a straight-chain alkoxy group having 1 to 5 C atoms,
and Ib-1 and Ib-2,

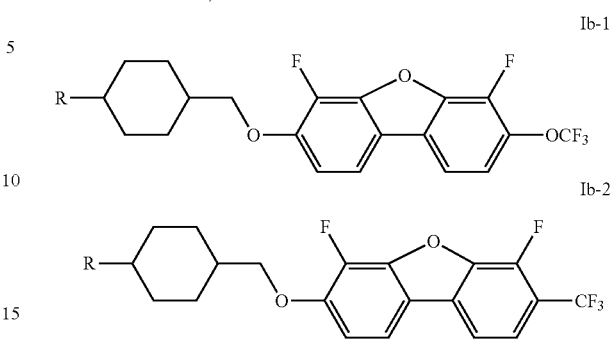

in which R denotes a straight-chain alkyl or alkenyl group having 2 to 5 C atoms.

Very particular preference is given to compounds of the formulae Ia-1-1 to Ia-1-8 and Ib-1-1 to Ib-1-5,

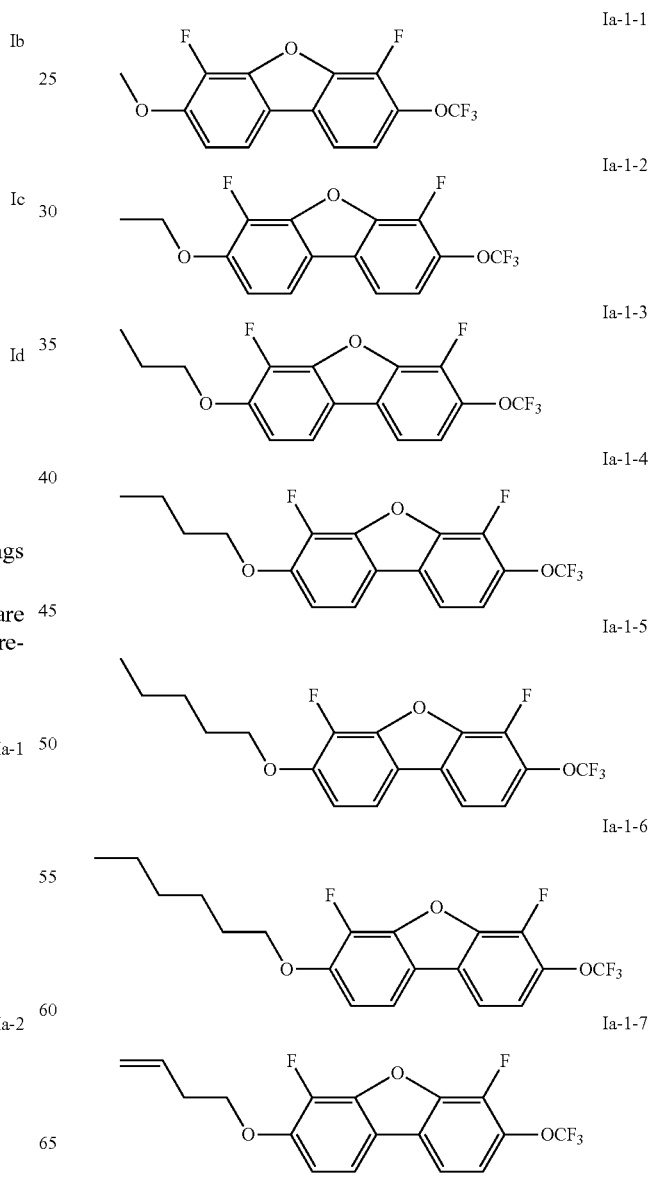

-continued

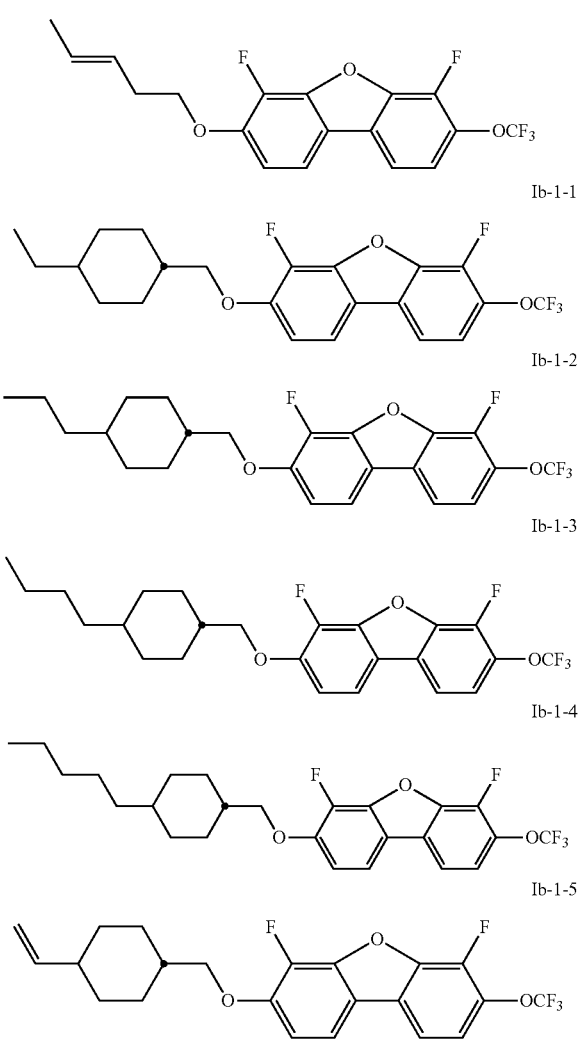

Ia-1-8
Ib-1-1
Ib-1-2
Ib-1-3
Ib-1-4
Ib-1-5

If radicals or substituents of the compounds according to the invention or the compounds according to the invention themselves are in the form of optically active or stereoisomeric radicals, substituents or compounds respectively since they have, for example, a centre of asymmetry, these are likewise encompassed by the present invention. In this case, the compounds of the general formula I according to the invention may exist in isomerically pure form, for example as pure enantiomers, diastereomers, E or Z isomers, trans or cis isomers, or as a mixture of a plurality of isomers in any desired ratio, for example as a racemate, E/Z isomer mixture or as a cis/trans isomer mixture.

The 1,4-substituted cyclohexyl ring of the formula

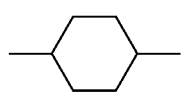

or -Cyc- in the compounds disclosed for liquid-crystalline media preferably has the trans configuration, i.e. the two substituents are both in the equatorial position in the thermodynamically preferred chair conformation.

The compounds of the general formula I can be prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can be made here of variants known per se which are not mentioned here in greater detail.

If desired, the starting materials can also be formed in situ by not isolating them from the reaction mixture, but instead immediately converting them further into the compounds of the general formula I.

The syntheses of compounds of the general formula I according to the invention are described by way of example in the examples. The starting substances can be obtained by generally accessible literature procedures or are commercially available.

Particularly suitable synthetic routes to the compounds according to the invention are explained below with reference to Scheme 1.

Scheme 1. Synthesis of the compounds of the formula I.

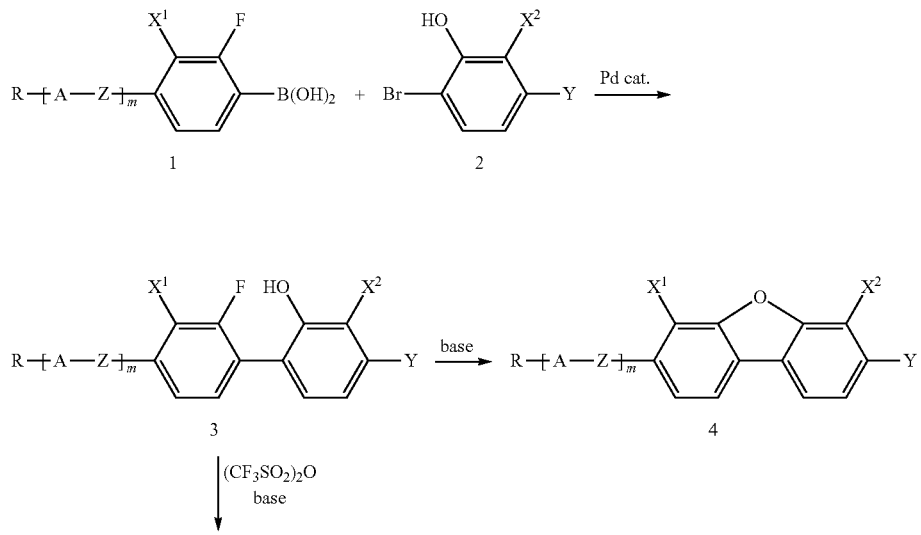

-continued

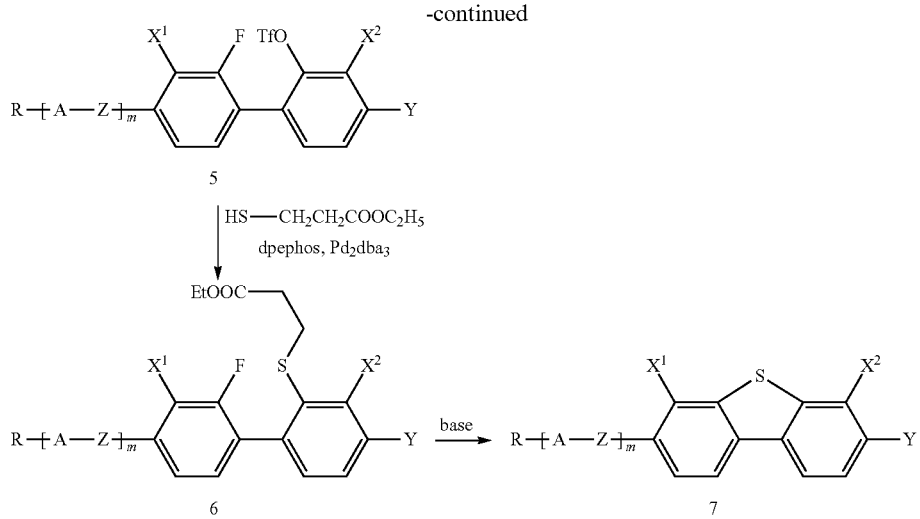

The radicals R, A, Z, X$^1$, X$^2$, Y and the index m have the meaning indicated for formula I.

Scheme 1 should only be regarded as illustrative. The person skilled in the art will be able to carry out corresponding variations of the syntheses presented, and also follow other suitable synthetic routes, in order to obtain compounds of the formula I.

In accordance with the synthesis depicted above, the present invention in an embodiment also encompasses one or more processes for the preparation of compounds of the formula I.

The invention thus encompasses a process for the preparation of compounds of the formula I which is characterised in that it comprises a process step in which a compound of the formula II is converted into compounds of the formula I in the presence of a base, as shown in Scheme 2 and in which R, A, Z, X$^1$, X$^2$, W and m have the meaning indicated above and G denotes —OH, —SH or SG' and G' denotes a base-labile protecting group for thiols. Preferred protecting groups are acetyl, dimethylaminocarbonyl, 2-tetrahydropyranyl, ethoxycarbonylethyl, tertbutyl, methyl, particularly preferably ethoxycarbonylethyl.

Scheme 2. Process for the preparation of the compounds of the formula I.

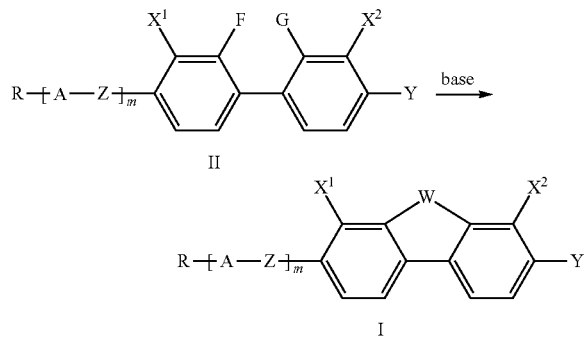

The process and the subsequent work-up of the reaction mixture can basically be carried out as a batch reaction or in a continuous reaction procedure. The continuous reaction procedure encompasses, for example, reaction in a continuous stirred-tank reactor, a stirred-reactor cascade, a loop or cross-flow reactor, a flow tube or in a microreactor. The reaction mixtures are optionally worked up, as necessary, by filtration via solid phases, chromatography, separation between immiscible phases (for example extraction), adsorption onto solid supports, removal of solvents and/or azeotropic mixtures by distillation, selective distillation, sublimation, crystallisation, co-crystallisation or by nanofiltration on membranes.

As already mentioned, the compounds of the general formula I can be used in liquid-crystalline media. The present invention therefore also relates to a liquid-crystalline medium comprising at least two liquid-crystalline compounds, comprising at least one compound of the general formula I.

The present invention also relates to liquid-crystalline media comprising 2 to 40, preferably 4 to 30, components as further constituents besides one or more compounds of the formula I according to the invention. These media particularly preferably comprise 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, 1,3-dioxanes, 2,5-tetrahydropyrans, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4',4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylethanes, 1-phenyl-2-cyclohexylphenylethanes, optionally halogenated stilbenes, benzyl phenyl ethers, tolans and substituted cinnamic acids. The 1,4-phenylene groups in these compounds may also be mono- or polyfluorinated.

The most important compounds suitable as further constituents of media according to the invention can be characterised by the formulae (II), (III), (IV), (V) and (VI):

R'-L-E-R" (II)

R'-L-COO-E-R" (III)

R'-L-OOC-E-R" (IV)

R'-L-CH$_2$CH$_2$-E-R" (V)

R'-L-CF$_2$O-E-R" (VI)

In the formulae (II), (III), (IV), (V) and (VI), L and E, which may be identical or different, each, independently of one another, denote a divalent radical from the group formed by -Phe-, -Cyc-, -Phe-Phe-, -Phe-Cyc-, -Cyc-Cyc-, -Pyr-, -Dio-, -Thp-, -G-Phe- and -G-Cyc- and their mirror images, where Phe denotes unsubstituted or fluorine-substituted 1,4-phenylene, Cyc denotes trans-1,4-cyclohexylene or 1,4-cyclohexenylene, Pyr denotes pyrimidine-2,5-diyl or pyridine-2,5-diyl, Dio denotes 1,3-dioxane-2,5-diyl, Thp denotes tetrahydropyran-2,5-diyl and G denotes 2-(trans-1,4-cyclo-hexyl)ethyl, pyrimidine-2,5-diyl, pyridine-2,5-diyl, 1,3-dioxane-2,5-diyl or tetrahydropyran-2,5-diyl.

One of the radicals L and E is preferably Cyc or Phe. E is preferably Cyc, Phe or Phe-Cyc. The media according to the invention preferably comprise one or more components selected from the compounds of the formulae (II), (III), (IV), (V) and (VI) in which L and E are selected from the group consisting of Cyc and Phe and simultaneously one or more components selected from the compounds of the formulae (II), (III), (IV), (V) and (VI) in which one of the radicals L and E is selected from the group consisting of Cyc and Phe and the other radical is selected from the group consisting of -Phe-Phe-, -Phe-Cyc-, -Cyc-Cyc-, -G-Phe- and -G-Cyc-, and optionally one or more components selected from the compounds of the formulae (II), (III), (IV), (V) and (VI) in which the radicals L and E are selected from the group consisting of -Phe-Cyc-, -Cyc-Cyc-, -G-Phe- and -G-Cyc-.

In a smaller sub-group of the compounds of the formulae (II), (III), (IV), (V) and (VI), R' and R" each, independently of one another, denote alkyl, alkenyl, alkoxy, alkoxyalkyl (oxaalkyl), alkenyloxy or alkanoyloxy having up to 8 C atoms. This smaller sub-group is called group A below, and the compounds are referred to by the sub-formulae (IIa), (IIIa), (IVa), (Va) and (VIa). In most of these compounds, R' and R" are different from one another, one of these radicals usually being alkyl, alkenyl, alkoxy or alkoxyalkyl (oxaalkyl).

In another relatively small sub-group of the compounds of the formulae (II), (III), (IV), (V) and (VI), known as group B, R" denotes —F, —Cl, —NCS or —(O)$_i$CH$_{3-k}$F$_k$, where i is 0 or 1 and k is 1, 2 or 3. The compounds in which R" has this meaning are denoted by the sub-formulae (IIb), (IIIb), (IVb), (Vb) and (VIb). Particular preference is given to compounds of the sub-formulae (IIb), (IIIb), (IVb), (Vb) and (VIb) in which R" has the meaning —F, —Cl, —NCS, —CF$_3$, —OCHF$_2$ or —OCF$_3$.

In the compounds of group B, which are referred to by the sub-formulae (IIb), (IIIb), (IVb), (Vb) and (VIb), R' is as defined for the compounds of the sub-formulae (IIa) to (VIa) and is preferably alkyl, alkenyl, alkoxy or alkoxyalkyl (oxaalkyl).

In a further smaller sub-group of the compounds of the formulae (II), (III), (IV), (V) and (VI), R" denotes —CN. This sub-group is referred to below as group C, and the compounds of this sub-group are correspondingly described by sub-formulae (IIc), (IIIc), (IVc), (Vc) and (VIc). In the compounds of the sub-formulae (IIc), (IIIc), (IVc), (Vc) and (VIc), R' is as defined for the compounds of the sub-formulae (IIa) to (VIa) and is preferably alkyl, alkenyl, alkoxy or alkoxyalkyl (oxaalkyl).

Besides the preferred compounds of groups A, B and C, other compounds of the formulae (II), (III), (IV), (V) and (VI) having other variants of the proposed substituents are also customary. All these substances are obtainable by methods which are known from the literature or analogously thereto.

Besides the compounds of the general formula I according to the invention, the media according to the invention preferably comprise one or more compounds from groups A, B and/or C. The proportions by weight of the compounds from these groups in the media according to the invention are:

Group A:
from 0 to 90%, preferably from 20 to 90%, in particular from 30 to 90%.
Group B:
from 0 to 80%, preferably from 10 to 80%, in particular from 10 to 70%.
Group C:
from 0 to 80%, preferably from 5 to 80%, in particular from 5 to 50%.

The media according to the invention preferably comprise from 1 to 40%, particularly preferably from 5 to 30%, by weight of the compounds of the formula I according to the invention, based on the total weight of the composition. The media preferably comprise one, two, three, four or five compounds of the formula I according to the invention.

The media according to the invention are prepared in a manner conventional per se. In general, the components are dissolved in one another, preferably at elevated temperature. By means of suitable additives, the liquid-crystalline phases of the present invention can be modified in such a way that they can be used in all types of liquid-crystal display element that have been disclosed hitherto. Additives of this type are known to the person skilled in the art and are described in detail in the literature (H. Kelker/R. Hatz, Handbook of Liquid Crystals, Verlag Chemie, Weinheim, 1980). For example, pleochroic dyes can be added for the production of coloured guest-host systems or substances can be added in order to modify the dielectric anisotropy, the viscosity and/or the alignment of the nematic phases.

Owing to their negative Δε, the compounds of the formula I are suitable for use in VA-TFT displays.

The value for ε⊥ of compounds of formula I is preferably in the range from 10 to 50, more preferably in the range from 15-40 and particularly preferably in the range from 18 to 30. Owing to their high value for ε⊥, the compounds of the formula I are particularly suitable for use in FFS-TFT displays.

The present invention therefore also relates to electro-optical liquid-crystal display elements containing a liquid-crystalline medium according to the invention.

Further combinations of the embodiments and variants of the invention in accordance with the description arise from the claims.

The invention is explained in greater detail below with reference to working examples, but without intending to be restricted thereby. The person skilled in the art will be able to glean from the examples working details that are not given in detail in the general description, generalise them in accordance with general expert knowledge and apply them to a specific problem.

Besides the usual and well-known abbreviations, the following abbreviations are used:

C: crystalline phase; N: nematic phase; Sm: smectic phase; I: isotropic phase. The numbers between these symbols show the transition temperatures of the substance concerned.

Temperature data are in ° C., unless indicated otherwise.

Physical, physicochemical or electro-optical parameters are determined by generally known methods, as described, inter alia, in the brochure "Merck Liquid Crystals—Licristal®—Physical Properties of Liquid Crystals—Description of the Measurement Methods", 1998, Merck KGaA, Darmstadt.

Above and below, Δn denotes the optical anisotropy (589 nm, 20° C.) and Δε denotes the dielectric anisotropy (1 kHz, 20° C.). The dielectric anisotropy Δε is determined at 20° C. and 1 kHz. The optical anisotropy Δn is determined at 20° C. and a wavelength of 589.3 nm.

The Δε and Δn values and the rotational viscosity ($\gamma_1$) of the compounds according to the invention are obtained by linear extrapolation from liquid-crystalline mixtures consisting of 5 to 10% of the respective compound according to the invention and 90-95% of the commercially available liquid-crystal mixture ZLI-2857 (for Δε) or ZLI-4792 (for Δn, $\gamma_1$) (mixtures, Merck KGaA, Darmstadt).

The abbreviations above and below have the following meanings:

DMAP 4-(N,N-dimethylamino)pyridine
DMPU 1,3-dimethyl-3,4,5,6-tetrahydro-2(1H)-pyrimidinone
dpephos bis[2-(diphenylphosphino)phenyl] ether
dba dibenzylideneacetone
n-BuLi n-butyllithium, solution in hexane
MTB ether methyl tert-butyl ether
THF tetrahydrofuran

EXAMPLES

The present invention is described in detail by the following non-restrictive examples.

Example 1: 4,6-Difluoro-3-trifluoromethoxy-7-pentyloxydibenzofuran 1.1: 1,2-Difluoro-3-pentyloxybenzene

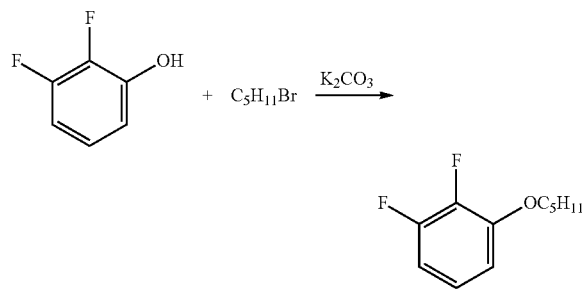

19.0 g (146 mmol) of 2,3-difluorophenol and 20.1 ml (163 mmol) of 1-bromopentane are dissolved in ethyl methyl ketone, 22.4 g of potassium carbonate are added, and the mixture is heated at the boil overnight. The solid is subsequently separated off, and the solvent is removed. The pentyl 2,3-difluorophenyl ether obtained is employed in the subsequent step without further purification.

1.2: 2,3-Difluoro-4-pentyloxybenzeneboronic acid

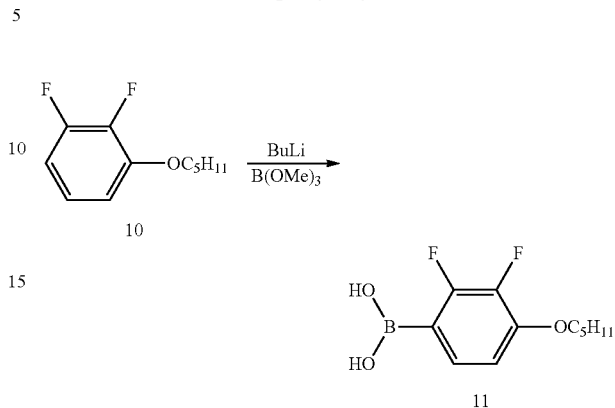

108 ml of a 15% solution of n-butyllithium in n-hexane (172 mmol) are added to a solution of 31.2 g of the crude product from step 1 (10) in 225 ml of THF at −70° C. After 1 h at this temperature, 20 ml (176 mmol) of trimethyl borate dissolved in 25 ml of THF are added. After a further hour, the batch is warmed to 0° C., water is added, and the mixture is adjusted to pH 1 using 25% hydrochloric acid. The aqueous phase is separated off and extracted with MTB ether. The combined organic phases are dried over sodium sulfate and evaporated. Crystallisation from n-heptane gives 2,3-difluoro-4-pentyloxybenzeneboronic acid as a colourless solid.

1.3: 6-Bromo-2-fluoro-3-trifluoromethoxyphenol

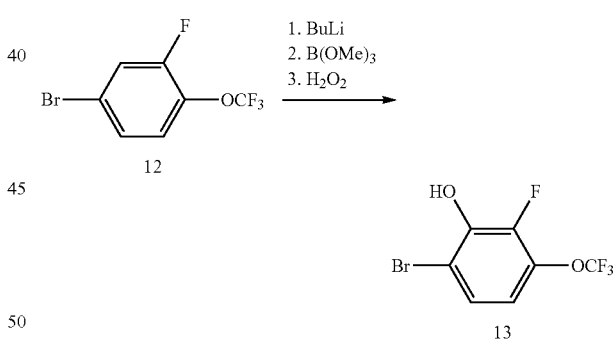

227 mmol of an LDA solution in 100 ml of THF, prepared from 32 ml of diisopropylamine and 143 ml of a 15% solution of n-butyllithium in n-hexane, are added to a solution of 33 ml (207 mmol) of 1-bromo-3-fluoro-4-trifluoromethoxybenzene (12) in 150 ml of THF at a temperature of −70° C. under nitrogen. After 1 h at the temperature, 26 ml (104 mmol) of trimethyl borate, dissolved in 50 ml of THF, are added to the batch. After a further hour, the batch is warmed to 0° C., and 30 ml of glacial acetic acid diluted with 38 ml of water are added. After 30 min. at room temp., 45 ml of a 35 percent hydrogen peroxide solution are added dropwise at a temperature between 35° C. and 40° C. After completion of the addition, the batch is kept at between 35° C. and 40° C. for 3 h, subsequently cooled to room temp., and water and MTB ether are added. The organic phase is washed with water and ammonium iron(II) sulfate solution, dried over sodium sulfate and evaporated. The residue is filtered through silica gel with n-pentane/dichloromethane, giving 6-bromo-2-fluoro-3-trifluoro-methoxyphenol as colourless oil.

1.4: 3,2',3'-Trifluoro-4'-pentyloxy-4-trifluoromethoxybiphenyl-2-ol

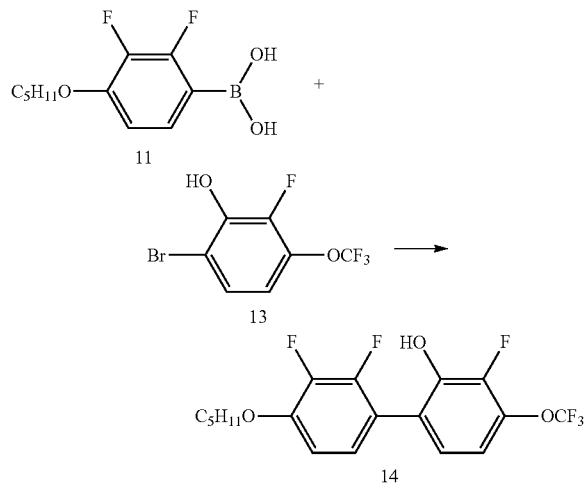

1.8 g (13 mmol) of potassium carbonate, 6 ml of water and, at about 60° C., 40 mg (4 mmol) of tris(dibenzylideneacetone)dipalladium(0) and 50 mg of di-(1-adamantyl)butylphosphine are added to a solution of 3 g (80%, 9 mmol) of 6-bromo-2-fluoro-3-trifluoromethoxyphenol (13) in 15 ml of THF under nitrogen, and the mixture is subsequently heated to the boil. A solution of 2.6 g (97%, 10 mmol) of 2,3-difluoro-4-pentyloxybenzeneboronic acid (11) in 10 ml of THF is added dropwise at the boiling point. The batch is heated under reflux overnight and cooled, water and MTB ether are added, and the mixture is acidified using dil. hydrochloric acid. The aqueous phase is extracted with MTB ether. The combined organic phases are dried over sodium sulfate and evaporated, and the residue is filtered through silica gel with toluene, giving 3,2',3'-trifluoro-4'-pentyloxy-4-trifluoromethoxybiphenyl-2-ol as colourless solid.

1.5: 4,6-Difluoro-3-trifluoromethoxy-7-pentyloxydibenzofuran

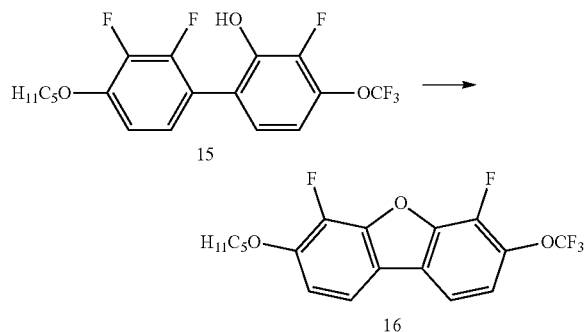

2.40 g (5.56 mmol) of 3,2',3'-trifluoro-4'-pentyloxy-4-trifluoromethoxy-biphenyl-2-ol and 15.5 g (6.60 mmol) of potassium triphosphate monohydrate are left to stir overnight at 110° C. in 20 ml of DMPU. After cooling, the batch is diluted with MTB ether, washed with water and sat. sodium chloride solution and dried over sodium sulfate. The crude product is chromatographed on silica gel with toluene and recrystallised from toluene, giving 4,6-difluoro-3-trifluoromethoxy-7-pentyloxydibenzofuran as colourless crystals of m.p. 68° C.

The following compounds are prepared analogously to Example 1:

| Ex. | R | M.p. [° C.] | $\varepsilon_\perp$ | $\Delta\varepsilon$ | $\Delta n$ | $\gamma_1$ [mPa·s] |
|---|---|---|---|---|---|---|
| 1 | n-C$_5$H$_{11}$ | 68 | 19.81 | −3.55 | 0.1361 | 68 |
| 2 | CH$_3$ | 112 | | | | |
| 3 | C$_2$H$_5$ | 112 | | | | |
| 4 | n-C$_3$H$_7$ | 97 | | | | |
| 5 | n-C$_4$H$_9$ | 87 | | | | |
| 6 | n-C$_6$H$_{13}$ | 72 | 20.84 | −5.40 | 0.1393 | 100 |

The compound

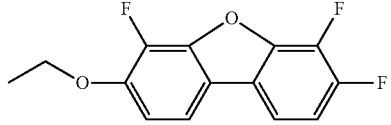

known from the prior art has the following values:
$\Delta\varepsilon = -7.79$
$\varepsilon_\perp = 24.69$
$\varepsilon_\perp / |\Delta\varepsilon| = 3.17$
For Example 1, $\varepsilon_\perp / |\Delta\varepsilon| = 5.58$ is obtained.
For Example 6, $\varepsilon_\perp / |\Delta\varepsilon| = 3.86$ is obtained.
The comparison shows that the compounds according to the invention have much higher and thus more advantageous values for the ratio of $\varepsilon_\perp$ to $|\Delta\varepsilon|$.

The following compounds are prepared analogously to Example 1:

| Ex. | R | M.p. [° C.] | $\varepsilon_\perp$ | $\Delta\varepsilon$ | $\Delta n$ | $\gamma_1$ [mPa·s] |
|---|---|---|---|---|---|---|
| 7 | CH$_3$ | | | | | |
| 8 | C$_2$H$_5$ | | | | | |
| 9 | n-C$_3$H$_7$ | | | | | |
| 10 | n-C$_4$H$_9$ | | | | | |
| 11 | n-C$_5$H$_{11}$ | 46 | 16.29 | −3.16 | 0.1113 | 59 |
| 12 | n-C$_6$H$_{13}$ | | | | | |

The following compounds are prepared analogously to Example 1:

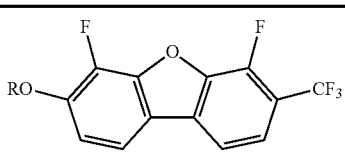

| Ex. | R | M.p. [° C.] | $\varepsilon_\perp$ | $\Delta\varepsilon$ | $\Delta n$ | $\gamma_1$ [mPa · s] |
|---|---|---|---|---|---|---|
| 13 | CH₃ | | | | | |
| 14 | C₂H₅ | | | | | |
| 15 | n-C₃H₇ | | | | | |
| 16 | n-C₄H₉ | | | | | |
| 17 | n-C₅H₁₁ | 74 | 23.66 | −2.99 | 0.1333 | 85 |
| 18 | n-C₆H₁₃ | 76 | 23.11 | −3.76 | 0.1333 | 89 |

The following compounds are prepared analogously to Example 1:

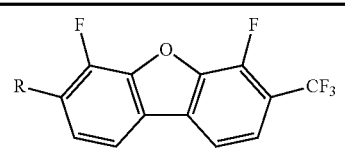

| Ex. | R | M.p. [° C.] | $\varepsilon_\perp$ | $\Delta\varepsilon$ | $\Delta n$ | $\gamma_1$ [mPa · s] |
|---|---|---|---|---|---|---|
| 19 | CH₃ | | | | | |
| 20 | C₂H₅ | | | | | |
| 21 | n-C₃H₇ | | | | | |
| 22 | n-C₄H₉ | | | | | |
| 23 | n-C₅H₁₁ | 46 | 18.84 | 2.17 | 0.1212 | 75 |
| 24 | n-C₆H₁₃ | | | | | |

Example 25: Butoxy-4,6-difluoro-7-trifluoromethoxydibenzothiophene

25.1: 3,2',3'-Trifluoro-4'-butyloxy-4-trifluoromethoxybiphenyl-2-ol

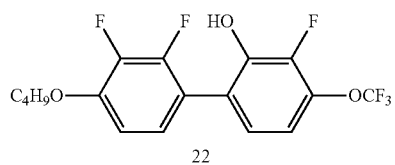

Phenol 22 is prepared analogously to compound 14 by a Suzuki coupling from compound 13 and commercially available 4-butoxy-2,3-difluoro-benzeneboronic acid.

25.2: 3,2',3'-Trifluoro-4'-butyloxy-4-trifluoromethoxybiphenyl-2-yl trifluoro-methanesulfonate

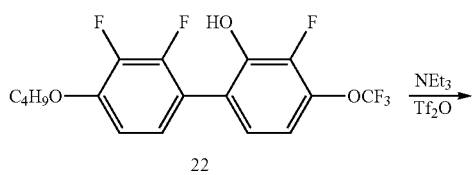

Triethylamine (5.0 ml) and DMAP (60 mg) are added dropwise to a solution of 3,2',3'-trifluoro-4'-butyloxy-4-trifluoromethoxybiphenyl-2-ol (9.7 g) in dichloromethane (70 ml). Trifluoromethanesulfonic anhydride (5.0 ml) is subsequently added dropwise at 5° C., and the reaction mixture is stirred at room temperature for 20 h. The mixture is filtered through silica gel, washed with dichloromethane, dried (Na₂SO₄) and evaporated in vacuo. 3,2',3'-Trifluoro-4'-butyloxy-4-trifluoromethoxybiphenyl-2-yl trifluoromethanesulfonate 9 is isolated as residue in the form of a pale-yellow oil.

25.3: Ethyl 3-(4'-butoxy-3,2',3'-trifluoro-4-trifluoromethoxybiphenyl-2-yl-sulfanyl)propionate

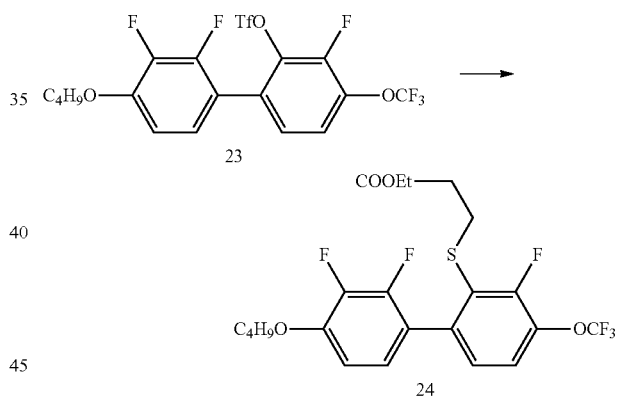

A solution of 3,2',3'-trifluoro-4'-butyloxy-4-trifluoromethoxybiphenyl-2-yl trifluoromethanesulfonate (12.7 g) and ethyl 3-mercaptopropionate (3.8 ml) in toluene (55 ml) is heated under reflux under a nitrogen atmosphere, and bis(2-diphenylphosphinophenyl) ether (1.3 g), tris(dibenzylidene-acetone)dipalladium(0) (1.2 g), potassium carbonate (8.4 g) and a small amount of dried molecular sieve are added. The reaction mixture is heated under reflux for 20 h and subsequently cooled, and MTB ether and dist. water are added. The organic phase is separated off, dried (Na₂SO₄) and evaporated in vacuo. Purification of the residue by column chromatography (eluent toluene) gives ethyl 3-(4'-butoxy-3,2',3'-trifluoro-4-trifluoro-methoxybiphenyl-2-yl-sulfanyl)propionate as yellow oil.

25.4: Butoxy-4,6-difluoro-7-trifluoromethoxydibenzothiophene

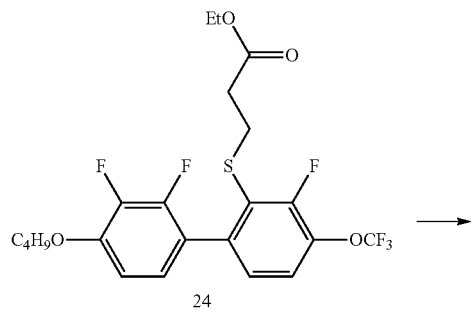

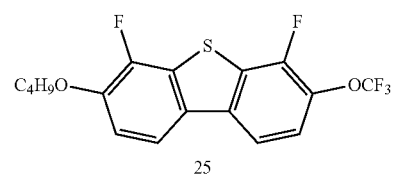

2.50 g (22.3 mmol) of potassium tert-butoxide are initially introduced in 30 ml of THF, and a solution of 9.20 g (18.3 mmol) of ethyl 3-(4'-butoxy-3,2',3'-trifluoro-4-trifluoromethoxybiphenyl-2-ylsulfanyl)propionate in 40 ml of THF is added dropwise at room temp. at such a rate that the temperature does not exceed 30° C. The batch is subsequently heated under reflux for 1 h, cooled, diluted with MTB ether and washed with water. The org. phase is dried over sodium sulfate, the solvent is removed in vacuo, and the residue is filtered through silica gel with toluene. Crystallisation of the crude product from ethanol gives 3-butoxy-4,6-difluoro-7-trifluoromethoxy-dibenzothiophene as colourless crystals of m.p. 121° C.

The following compounds are prepared analogously to Example 25:

| Ex. | R | M.p. [° C.] | $\varepsilon_\perp$ | $\Delta\varepsilon$ | $\Delta n$ | $\gamma_1$ [mPa·s] | Phase sequence |
|---|---|---|---|---|---|---|---|
| 25 | n-C$_4$H$_9$ | 121 | | | | | |
| 26 | CH$_3$ | | | | | | |
| 27 | C$_2$H$_5$ | 135 | | | | | |
| 28 | n-C$_3$H$_7$ | 138 | | | | | |
| 29 | n-C$_5$H$_{11}$ | 94 | 17.92 | −3.97 | 0.1413 | 103 | C 94 SmA 105 I |
| 30 | n-C$_6$H$_{13}$ | 114 | | | | | |

The following compounds are prepared analogously to Example 25:

| Ex. | R | M.p. [° C.] | $\varepsilon_\perp$ | $\Delta\varepsilon$ | $\Delta n$ | $\gamma_1$ [mPa·s] |
|---|---|---|---|---|---|---|
| 31 | CH$_3$ | | | | | |
| 32 | C$_2$H$_5$ | | | | | |
| 33 | n-C$_3$H$_7$ | | | | | |
| 34 | n-C$_4$H$_9$ | | | | | |
| 35 | n-C$_5$H$_{11}$ | 76 | | | | |
| 36 | n-C$_6$H$_{13}$ | | | | | |

The following compounds are prepared analogously to Example 25:

| Ex. | R | M.p. [° C.] | $\varepsilon_\perp$ | $\Delta\varepsilon$ | $\Delta n$ | $\gamma_1$ [mPa·s] |
|---|---|---|---|---|---|---|
| 37 | CH$_3$ | | | | | |
| 38 | C$_2$H$_5$ | | | | | |
| 39 | n-C$_3$H$_7$ | | | | | |
| 40 | n-C$_4$H$_9$ | | | | | |
| 41 | n-C$_5$H$_{11}$ | 53 | 19.10 | 5.37 | 0.1293 | 81 |
| 42 | n-C$_6$H$_{13}$ | | | | | |

The following compounds are prepared analogously to Example 25:

| Ex. | R | M.p. [° C.] | $\varepsilon_\perp$ | $\Delta\varepsilon$ | $\Delta n$ | $\gamma_1$ [mPa·s] |
|---|---|---|---|---|---|---|
| 43 | CH$_3$ | | | | | |
| 44 | C$_2$H$_5$ | | | | | |
| 45 | n-C$_3$H$_7$ | | | | | |
| 46 | n-C$_4$H$_9$ | | | | | |
| 47 | n-C$_5$H$_{11}$ | 75 | | | 0.1492 | 84 |
| 48 | n-C$_6$H$_{13}$ | | | | | |

The following compounds are prepared analogously to Example 25:

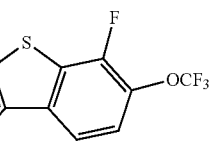

| Ex. | R | M.p. [° C.] | $\varepsilon_\perp$ | $\Delta\varepsilon$ | $\Delta n$ | $\gamma_1$ [mPa·s] |
|---|---|---|---|---|---|---|
| 49 | CH$_3$ | | | | | |
| 50 | C$_2$H$_5$ | | | | | |
| 51 | n-C$_3$H$_7$ | | | | | |

-continued

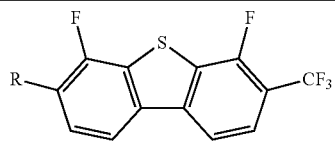

| Ex. | R | M.p. [° C.] | $\varepsilon_\perp$ | $\Delta\varepsilon$ | $\Delta n$ | $\gamma_1$ [mPa·s] |
|---|---|---|---|---|---|---|
| 52 | n-C$_4$H$_9$ | | | | | |
| 53 | n-C$_5$H$_{11}$ | 65 | | | | |
| 54 | n-C$_6$H$_{13}$ | | | | | |

The following compounds are prepared analogously to Example 25:

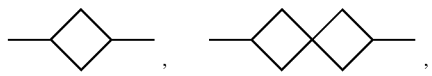

| Ex. | R | M.p. [° C.] | $\varepsilon_\perp$ | $\Delta\varepsilon$ | $\Delta n$ | $\gamma_1$ [mPa·s] |
|---|---|---|---|---|---|---|
| 55 | CH$_3$ | | | | | |
| 56 | C$_2$H$_5$ | | | | | |
| 57 | n-C$_3$H$_7$ | | | | | |
| 58 | n-C$_4$H$_9$ | | | | | |
| 59 | n-C$_5$H$_{11}$ | 112 | | | | |
| 60 | n-C$_6$H$_{13}$ | | | | | |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German Patent Application No. DE 10 2015 004 505.9, filed Apr. 13, 2015 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. A compound of the formula I

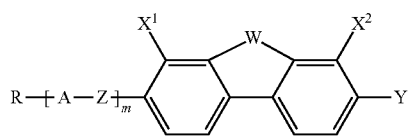

I in which
W denotes O or S,
Y denotes F, Cl, CF$_3$, OCF$_3$ or OCF$_2$H,
  with the proviso that, if W denotes O, Y cannot be F,
X$^1$, X$^2$ denote H or F,
  with the proviso that at least one radical X$^1$ or X$^2$ denotes F,
R denotes an alkyl or alkoxy radical having 1 to 15 C atoms, where, in addition, one or more CH$_2$ groups in these radicals may each be replaced, independently of one another, by —C≡C—, —CF$_2$O—, —OCF$_2$—, —CH=CH—, —O—, —CO—O— or —O—CO— in such a way that O atoms are not linked directly to one another, and in which, in addition, one or more H atoms may be replaced by halogen,
A on each occurrence, identically or differently, denotes a radical selected from the following groups:
  a) 1,4-phenylene, in which, in addition, one or two CH groups may be replaced by N and in which, in addition, one or more H atoms may be replaced by a group L,
  b) the group consisting of trans-1,4-cyclohexylene and 1,4-cyclohexenylene, in which, in addition, one or more non-adjacent CH$_2$ groups may be replaced by —O— and/or —S— and in which, in addition, one or more H atoms may be replaced by F or Cl, and
  c) the group consisting of tetrahydropyran-2,5-diyl, 1,3-dioxane-2,5-diyl, tetrahydrofuran-2,5-diyl, cyclobutane-1,3-diyl, piperidine-1,4-diyl, thiophene-2,5-diyl and selenophene-2,5-diyl, each of which may also be mono- or polysubstituted by a group L,
L on each occurrence, identically or differently, denotes F, Cl, CN, SCN, SF$_5$ or straight-chain or branched, and in each case optionally fluorinated alkyl, alkoxy, alkylcarbonyl, alkoxycarbonyl, alkylcarbonyloxy or alkoxycarbonyloxy having 1 to 12 C atoms, and
Z on each occurrence, identically or differently, denotes a single bond, —CF$_2$O—, —OCF$_2$—, —CH$_2$O—, —OCH$_2$—, —(CO)O—, —O(CO)—, —(CH$_2$)$_4$—, —CH$_2$CH$_2$—, —CF$_2$—CF$_2$—, —CF$_2$—CH$_2$—, —CH$_2$—CF$_2$—, —CH=CH—, —CF=CF—, —CF=CH—, —CH=CF—, —(CH$_2$)$_3$O—, —O(CH$_2$)$_3$—, —C≡C—, —O—, —CH$_2$—, —(CH$_2$)$_3$— or —CF$_2$—,
m denotes 0, 1 or 2.

2. A compound according to claim 1, wherein X$^1$ and X$^2$ both denote F.

3. A compound according to claim 1, wherein m denotes 0 or 1.

4. A compound according to claim 1, wherein Y in formula I denotes CF$_3$ or OCF$_3$.

5. A compound according to claim 4, wherein Y denotes OCF$_3$.

6. A compound according to claim 1, wherein the compound of the formula I is selected from the compounds of sub-formulae Ia to Id,

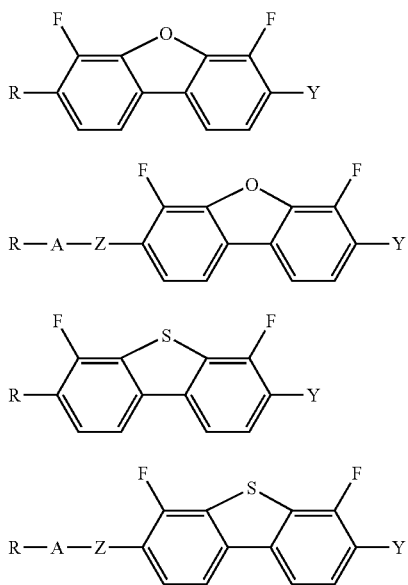

in which R, A, Z and Y have the meanings indicated for formula I in claim 1.

7. A compound according to claim 1, wherein W denotes O.

8. A compound according to claim 1, wherein the compound is selected from the compounds of the following formulae:

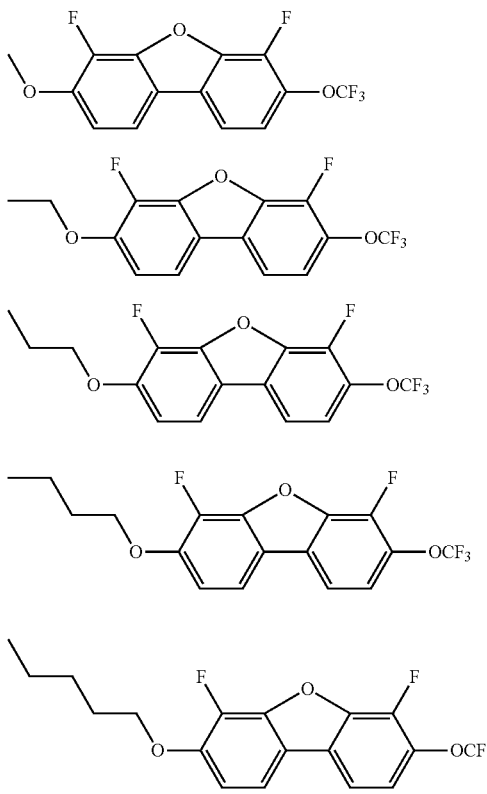

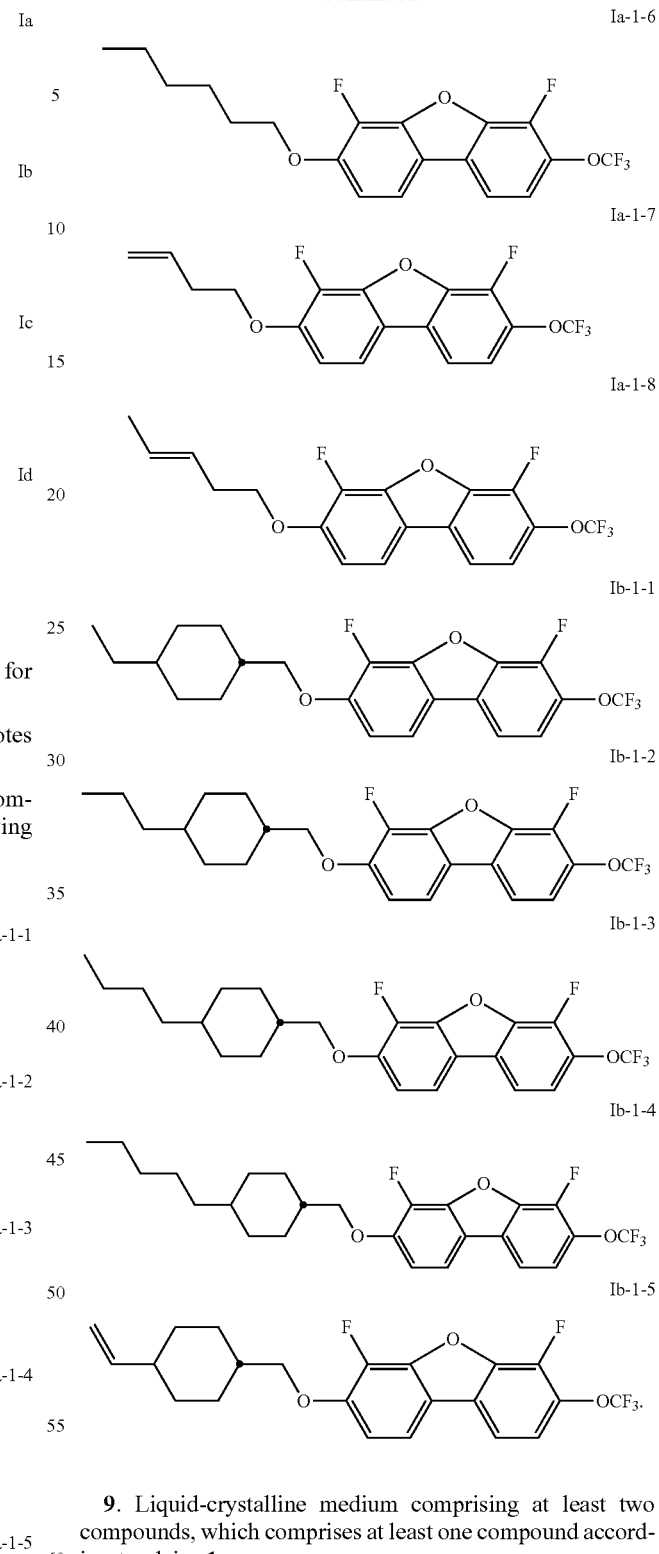

9. Liquid-crystalline medium comprising at least two compounds, which comprises at least one compound according to claim 1.

10. Electro-optical display element containing a liquid-crystalline medium according to claim 9.

11. Process for the preparation of a compound of the formula I according to claim 1, comprising converting a compound of the formula II into a compound of the formula I

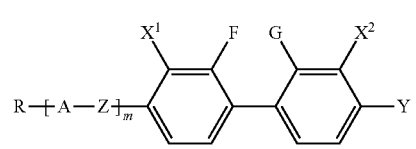
where R, A, Z, $X^1$, $X^2$, W, Y and m have the meaning indicated under claim 1 and G denotes —OH or —SG', where G' denotes H or a protecting group.
* * * * *